United States Patent
Ho et al.

(10) Patent No.: US 12,097,229 B1
(45) Date of Patent: *Sep. 24, 2024

(54) PROCESS OF MANUFACTURING COMPOSITION FOR THE PREVENTION AND TREATMENT OF EARLY MORTALITY SYNDROME (EMS) SHRIMP

(71) Applicant: Vien Anh Xuan Ho, Ho Chi Minh (VN)

(72) Inventors: Vien Anh Xuan Ho, Ho Chi Minh (VN); Anh Dang Tran, Ho Chi Minh (VN)

(73) Assignee: VIEN ANH XUAN HO, Ho Chi Minh (VN)

( * ) Notice: Subject to any disclaimer, the term of this patent is extended or adjusted under 35 U.S.C. 154(b) by 0 days.

This patent is subject to a terminal disclaimer.

(21) Appl. No.: 18/594,014

(22) Filed: Mar. 4, 2024

Related U.S. Application Data

(63) Continuation-in-part of application No. 18/592,551, filed on Mar. 1, 2024.

(51) Int. Cl.
| | | |
|---|---|---|
| *A61K 36/07* | (2006.01) | |
| *A61K 36/53* | (2006.01) | |
| *A61K 36/61* | (2006.01) | |
| *A61K 36/79* | (2006.01) | |
| *A61K 47/02* | (2006.01) | |
| *A61K 47/10* | (2017.01) | |
| *A61K 47/12* | (2006.01) | |
| *A61K 47/18* | (2017.01) | |
| *A61K 47/22* | (2006.01) | |
| *A61K 47/26* | (2006.01) | |
| *A61K 47/38* | (2006.01) | |
| *A61P 31/04* | (2006.01) | |
| *C12N 1/14* | (2006.01) | |

(52) U.S. Cl.
CPC .............. *A61K 36/07* (2013.01); *A61K 36/53* (2013.01); *A61K 36/61* (2013.01); *A61K 36/79* (2013.01); *A61K 47/02* (2013.01); *A61K 47/10* (2013.01); *A61K 47/12* (2013.01); *A61K 47/183* (2013.01); *A61K 47/22* (2013.01); *A61K 47/26* (2013.01); *A61K 47/38* (2013.01); *A61P 31/04* (2018.01); *C12N 1/145* (2021.05); *A61K 2236/11* (2013.01); *A61K 2236/15* (2013.01); *A61K 2236/17* (2013.01); *A61K 2236/331* (2013.01); *A61K 2236/37* (2013.01); *A61K 2236/53* (2013.01); *A61K 2236/55* (2013.01)

(58) Field of Classification Search
None
See application file for complete search history.

*Primary Examiner* — Russell G Fiebig

(57) ABSTRACT

A composition for prevention and treatment of Early Mortality Syndrome (EMS) shrimp to replace antibiotics obtain from process creating a basic mixture by mixing a complex composition with mixing ingredients, then stirring the basic mixture for 1 hour, and adjusting the pH to 6.5-7.5 and leaving it for one day at a temperature of 30° C.-35° C.; wherein the complex composition including 10%-15% by weight of a turkey tail mushroom extract and 10%-15% by weight of a chitosan; in which mixing ingredients consisting of a carboxymethyl cellulose solution 0.375%, a alginate solution 0.375%, a potassium citrate solution, a $AgNO_3$ solution 0.37%, a $Cu(NO_3)_2$ solution 0.723%, a $Zn(NO_3)_2$ solution 3.085%, $Co(NO_3)_2$ solution 0.746%, a $Fe(NO_3)_3$ solution 2.5%, a glycerin ingredient, a vitamin E, a tartrazine ingredient 1%, a $K_2HPO_4$ solution 15%, a mixture extracts/essential oils, and an other ingredient.

16 Claims, 1 Drawing Sheet

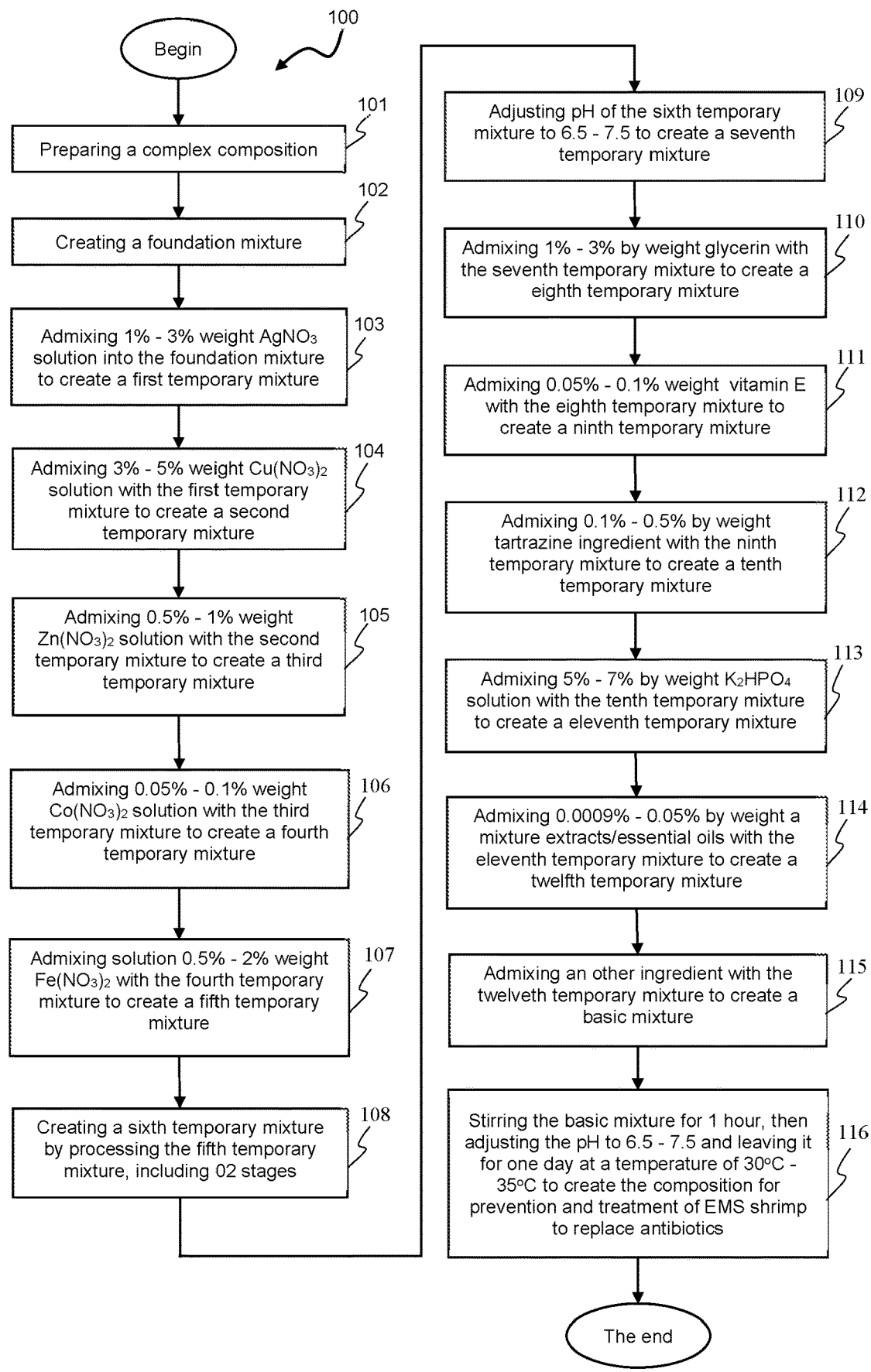

PROCESS OF MANUFACTURING COMPOSITION FOR THE PREVENTION AND TREATMENT OF EARLY MORTALITY SYNDROME (EMS) SHRIMP

CLAIM OF PRIORITY

This application is a continuation application of application Ser. No. 18/592,551, entitled "A method for producing a complex composition of turkey tail mushroom extract—chitosan", filed on Mar. 1, 2024 (Mar. 1, 2024). The patent application identified above is incorporated here by reference in its entirety to provide continuity of disclosure.

FIELD OF THE INVENTION

The present invention relates to the field of aquaculture, specifically relating to a process of manufacturing composition for the prevention and treatment of Early Mortality Syndrome (EMS) shrimp to replace antibiotics, helps shrimp grow well, strengthens the immune system, and inhibits disease-causing bacteria. More specifically, the present invention relates to a process of manufacturing composition for the prevention and treatment of Early Mortality Syndrome (EMS) shrimp.

BACKGROUND ART

In recent years, shrimp farming has faced many difficulties and challenges, including diseases and environmental pollution of farming water, leading to mass shrimp deaths on a large scale. There are many causes leading to this phenomenon, but one of the initial causes identified is acute hepatopancreatic necrosis disease (AHPND), also known as early mortality syndrome (EMS). This disease is caused by gram-negative bacteria *Vibrio parahaemolyticus* (*V. parahaemolyticus*). The toxins of these bacterial strains destroy the hepatopancreatic system and cause a mortality rate of up to 100% in shrimp 30-35 days after stocking. Currently, disinfectant chemicals, antibiotics, and biological products are used to prevent and treat Early Mortality Syndrome—EMS. However, antibiotics and disinfectants cause unwanted effects on the environment and animal health, the quality of aquatic products, and the effectiveness of the treatment process.

Today, there is a trend of researching and using natural compounds originating from plants with antibacterial activity and especially high safety to replace commonly used antibiotics be resistant. Given the situation of overuse of antibiotics in aquaculture activities, which has caused drug resistance in pathogenic bacteria, the extraction of biologically active substances from plants has become one of the new approaches. Replacing the current use of antibiotics not only limits animal diseases and contributes to the development of sustainable aquaculture but is also safe for consumers as well as friendly to the ecological environment.

According to Patent No. WO2023017493A1, the invention refers to feed compositions for feeding aquatic organisms, characterised by the immunostimulant effect thereof. The immunostimulant feed compositions of the invention comprise prebiotic fibers of plant origin between 0.001 to 1% w/w; carbohydrates between 5 to 45% w/w; proteins between 15 to 50% w/w; fats between 1 to 15% w/w; and additives between 0.1% to 20% p/p. Wherein the composition is optionally coated with binders at a ratio between 0.1% w/w to 10% w/w and the binder is selected from starches, sago palm, cassava, potato, wheat flour, rice flour, corn flour, lignosulfonates, hemicellulose and carboxymethylcellulose, alginates, carrageenan, guar gum, locust bean gum, gum acacia, agar, chitosan, propylene glycol alginate, gelatin, and mixtures thereof.

According to Patent No. WO2019088770A2, the invention refers to a composition for alleviation of *Vibrio*-caused infectious disease in shrimp aquaculture and, more particularly, to a composition comprising a *Schisandra chinensis* extract and/or a *Cinnamomum cassia* extract as an effective ingredient for alleviation of *Vibrio* species infection. In the present invention, the *Vibrio* species includes *Vibrio parahaemolyticus* and *Vibrio harveyi*. Comprising a *Schisandra chinensis* extract and/or a *Cinnamomum cassia* extract as an effective ingredient, the composition for alleviation of early mortality syndrome and/or acute hepato-pancreatic necrosis disease attributed to infection of the bacteria exhibited antibacterial activity efficacy against *Vibrio* stains causing infection symptoms.

According to Patent No. KR11019043711B1, the invention refers to a composition for treating or preventing acute hepatopancreatic necrosis of shrimp comprising an ethanol extract of a herbal medicinal product comprising *Artemisia iwayomogi* and/or *Angelica gigas* as an active ingredient. The composition and the treatment or prevention method according to the present invention are excellent in an effect of killing or inhibiting the proliferation of *Vibrio parahaemolyticus* of shrimp, are excellent in the treatment and prevention of acute hepatopancreatic necrosis of shrimp, are safe as herbal components with no side effects on shrimp, and can be orally administered together with feed, thereby being usefully used in the aquaculture industry.

The above inventions meet the specific purposes and requirements of a technical solution. However, the above inventions only refer to composition for the prevention and treatment of Early Mortality Syndrome (EMS) shrimp, but the disclosure of the invention does not in detail the processes for preparing ingredients and steps for mixing and preparing to create a composition for the prevention and treatment of Early Mortality Syndrome (EMS) shrimp. More especially, the disclosure of the invention does not in detail the chemical ingredients of the composition incubation mixture containing components consisting of a complex composition include turkey tail mushroom extract having 10%-15% by weight and chitosan having 10%-15% by weight, a carboxymethyl cellulose solution has a concentration of 0.375% having 10%-15% by weight, a alginate solution has a concentration of 0.375% having 10%-15% by weight, a potassium citrate solution having 10%-15% by weight, an $AgNO_3$ solution has a concentration of 0.37% having 1%-3% by weight, a $Cu(NO_3)_2$ solution has a concentration of 0.723% having 3% 5% by weight, an $Zn(NO_3)_2$ solution has a concentration of 3.085% having 0.5%-1% by weight, a $Co(NO_3)_2$ solution has a concentration of 0.746% having 0.05%-0.1% by weight, a $Fe(NO_3)_3$ solution has a concentration of 2.5% having 0.5%-2% by weight, a glycerin having 1%-3% by weight, a vitamin E having 0.05%-0.1% by weight, a tartrazine has a concentration of 1% having 0.1%-0.5% by weight, a $K_2HPO_4$ solution has a concentration of 15% having 5%-7% by weight, an essential oil mixture having 0.0009%-0.05% by weight, and an other ingredient.

Therefore, it is necessary to create a process of manufacturing composition to prevent and treat Early Mortality Syndrome (EMS) shrimp to replace antibiotics, including simple, easy-to-follow steps.

Finally, It is necessary to create a manufacturing composition to prevent and treat Early Mortality Syndrome (EMS)

shrimp to replace antibiotics, enhance food absorption, stimulate digestion, enhance the immune system, and increase the survival rate for shrimp.

The invention provides solutions to achieve the above objectives.

SUMMARY OF THE INVENTION

Accordingly, an objective of the present invention is to provide a composition for prevention and treatment of Early Mortality Syndrome (EMS) shrimp to replace antibiotics obtain from process creating a basic mixture by mixing a complex composition with mixing ingredients, then stirring the basic mixture for 1 hour, and adjusting the pH to 6.5-7.5 and leaving it for one day at a temperature of 30° C.-35° C.; wherein the complex composition including 10%-15% by weight of a turkey tail mushroom extract and 10%-15% by weight of a chitosan; and in which said mixing ingredients consisting of a carboxymethyl cellulose solution has a concentration of 0.375%, a alginate solution has a concentration of 0.375%, a potassium citrate solution, a $AgNO_3$ solution has a concentration of 0.37%, a $Cu(NO_3)_2$ solution has a concentration of 0.723%, a $Zn(NO_3)_2$ solution has a concentration of 3.085%, $Co(NO_3)_2$ solution has a concentration of 0.746%, a $Fe(NO_3)_3$ solution has a concentration of 2.5%, a glycerin ingredient, a vitamin E, a tartrazine ingredient has a concentration of 1%, a $K_2HPO_4$ solution has a concentration of 15%, a mixture extracts/essential oils, and an other ingredient.

Another objective of the present invention is to provide a composition for prevention and treatment of Early Mortality Syndrome (EMS) shrimp comprising:
the complex composition including 10%-15% by weight of a turkey tail mushroom extract and 10%-15% by weight of a chitosan;
the carboxymethyl cellulose solution having 10%-15% by weight;
the alginate solution having 10%-15% by weight;
the potassium citrate solution having 10%-15% by weight;
the $AgNO_3$ solution having 1%-3% by weight;
the $Cu(NO_3)_2$ solution having 3%-5% by weight;
the $Zn(NO_3)_2$ solution having 0.5%-1% by weight;
the $Co(NO_3)_2$ solution having 0.05%-0.1% by weight;
the $Fe(NO_3)_3$ solution having 0.5%-2% by weight;
the glycerin ingredient having 1%-3% by weight;
the vitamin E having 0.05%-0.1% by weight;
the tartrazine ingredient having 0.1%-0.5% by weight;
the $K_2HPO_4$ solution having 5%-7% by weight;
the mixture extracts/essential oils having 0.0009%-0.05% by weight; wherein the mixture extracts/essential oils is obtained by mixing homogeneously a *Melaleuca alternifolia* extracts/essential oils with a Herba Pogostemonis extracts/essential oils and a *Illicium verum* extracts/essential oils at a ratio of (1-2):(1-2):(1-2); and the rest is other ingredient; wherein the other ingredient is selected from the group consisting of water, EDTA.4 Na, and combinations thereof.

Another objective of the present invention is to provide a composition for prevention and treatment of Early Mortality Syndrome (EMS) shrimp comprising:
the complex composition including 13%-13.5% by weight the turkey tail mushroom extract and 13%-13.5% by weight the chitosan;
the carboxymethyl cellulose solution having 13%-13.5% by weight;
the alginate solution having 13%-13.5% by weight;
the potassium citrate solution having 13%-13.5% by weight;
the $AgNO_3$ solution having 2.16% by weight;
the $Cu(NO_3)_2$ solution having 4.2%-4.5% by weight;
the $Zn(NO_3)_2$ solution having 0.9% by weight;
the $Co(NO_3)_2$ solution having 0.08% by weight;
the $Fe(NO_3)_3$ solution having 1.3%-1.5% by weight;
the glycerin ingredient having 2% by weight;
the vitamin E having 0.07%-0.08% by weight;
the tartrazine ingredient having 0.15%-0.2% by weight;
the $K_2HPO_4$ solution having 6.4%-6.8% by weight;
the mixture extracts/essential oils having 0.0009%-0.05% by weight; wherein the mixture extracts/essential oils is obtained by mixing homogeneously the *Melaleuca alternifolia* extracts/essential oils with the Herba Pogostemonis extracts/essential oils and the *Illicium verum* extracts/essential oils at a ratio of 1:1:1; and the rest is other ingredient; wherein the other ingredient is selected from the group consisting of water, EDTA.4 Na, and combinations thereof.

Another objective of the present invention is to provide a process of manufacturing composition for prevention and treatment of Early Mortality Syndrome (EMS) shrimp to replace antibiotics comprising:
(i) preparing a complex composition by mixing a turkey tail mushroom extract having 10%-15% by weight and a chitosan having 10%-15% by weight with the combination of stirring at 1200-1500 rpm for 30-40 minutes, then ultrasonic treatment at a frequency of 0.15 to 0.2 kHz combination of stirring at 1200-1500 rpm for 30-50 minutes;
wherein the chitosan having a minimum deacetylation level of 85% and is extracted from crustacean shells;
wherein the turkey tail mushroom extract is selecting from group consisting of (A) a first turkey tail mushroom component, (B) a second turkey tail mushroom component, (C) a third turkey tail mushroom component, (D) a fourth turkey tail mushroom component, and (E) a fifth turkey tail mushroom component;
the first turkey tail mushroom component is obtained by cultivating *Trametes versicolor* (L.) Pilat;
the second turkey tail mushroom component is obtained by cultivating *Trametes versicolor* (L.) Lioud (1920);
the third turkey tail mushroom component is obtained by cultivating *Trametes sanguinea* (L.) Imazeki;
the fourth turkey tail mushroom component is obtained by cultivating *Trametes versicolor* BRGO4; and
the fifth turkey tail mushroom component is obtained by cultivating *Pycnoporus sanguineus* (L.: Fr.) Murrill;
wherein each turkey tail mushroom component (A)-(E) is obtained by performing steps (A') to (F'), comprising:
(A') selecting a mature fruiting bodies of the turkey tail mushroom;
(B') harvesting mushroom tissue from the mature fruiting bodies of the turkey tail mushroom with an area ranging from 5-10 $mm^2$, inoculating onto a petri dish containing a isolation medium, and then incubating in darkness at 28° C.-30° C. for 4-6 days to obtain a turkey tail mushroom strain;

wherein the isolation medium comprising: potatoes having 200 g/L, glucose having 20 g/L, potassium dihydrogen phosphate ($KH_2PO_4$) having 3 g/L, magnesium sulfate ($MgSO_4$) having 1.5 g/L, and agar having 20 g/L;

(C') inoculating the turkey tail mushroom strain into an erlenmeyer flask containing 100-150 mL of an activation medium, shaking at 120-150 rpm for 4-6 days at 25° C.-27° C. to obtain an activated turkey tail mushroom strain;

wherein the activation medium comprising: glucose having 10 g/L, malt extract having 3 g/L, peptone having 2 g/L, yeast extract having 2 g/L, asparagine having 1 g/L, potassium dihydrogen phosphate ($KH_2PO_4$) having 2 g/L, magnesium sulfate ($MgSO_4$) having 1 g/L, and thiamine having 1 mg/L;

(D') inoculating the activated turkey tail mushroom strain into a biomass growth medium at a ratio of (1-5): 1000, cultivating with agitation at 120-150 rpm for 6-8 days at 25° C.-27° C. to obtain a mixture 1;

wherein the biomass growth medium comprising: glucose having 30 g/L, peptone having 4 g/L, magnesium sulfate ($MgSO_4$) having 0.5 g/L, and potassium dihydrogen phosphate ($KH_2PO_4$) having 1 g/L;

(E') filtering the mixture 1, removing the liquid portion to obtain a turkey tail mushroom biomass; and (F') drying the turkey tail mushroom biomass at 45° C.-50° C. until reaching a moisture content of 10-12% to obtain a turkey tail mushroom biomass component;

(ii) mixing 10%-15% by weight a carboxymethyl cellulose solution with 10%-15% by weight a alginate solution, and 10%-15% by weight a potassium citrate solution into the container containing the complex composition at step (i) with the combination of stirring for 30 minutes to create a foundation mixture;

wherein the carboxymethyl cellulose solution has a concentration of 0.375%;

wherein the alginate solution has a concentration of 0.375%;

wherein the potassium citrate solution is prepared by:

(a) preparing citric acid solution has a concentration of 15% by dissolving 1.5 kg of citric acid in the water, then continue adding water to reach the volume of 10 L;

(b) preparing potassium hydroxide (KOH) solution has a concentration of 15% by: dissolving 1.5 kg of KOH in the water, then continue adding water to reach the volume of 10 L; and (c) pouring slowly 1 part citric acid solution at step (a) into 1 part potassium hydroxide solution to create the potassium citrate solution;

(iii) mixing 1%-3% by weight a $AgNO_3$ solution into the foundation mixture at step (ii) with the combination of stirring to create a first temporary mixture; wherein the $AgNO_3$ solution has a concentration of 0.37%;

(iv) mixing 3%-5% by weight a $Cu(NO_3)_2$ solution into the first temporary mixture at step (iii) with the combination of stirring to create a second temporary mixture; wherein the $Cu(NO_3)_2$ solution has a concentration of 0.723%;

(v) mixing 0.5%-1% by weight a $Zn(NO_3)_2$ solution into the second temporary mixture at step (iv) with the combination of stirring to create a third temporary mixture; wherein the $Zn(NO_3)_2$ solution has a concentration of 3.085%;

(vi) mixing 0.05%-0.1% by weight a $Co(NO_3)_2$ solution into the third temporary mixture at step (v) with the combination of stirring to create a fourth temporary mixture; wherein the $Co(NO_3)_2$ solution has a concentration of 0.746%;

(vii) mixing 0.5%-2% by weight a $Fe(NO_3)_3$ solution into the fourth temporary mixture at step (vi) with the combination of stirring to create a fifth temporary mixture; wherein the $Fe(NO_3)_3$ solution has a concentration of 2.5%;

(viii) creating a sixth temporary mixture by processing the fifth temporary mixture at step (vii) including 02 stages:

a first stage: stirring the fifth temporary mixture for 1 hour; and a second stage: stirring said processed fifth temporary mixture in first stage at a frequency of every 3 hours and each time stirring for 30 minutes at a speed of 300-500 rpm; wherein the second stage processing time is 24 hours;

(ix) adjusting pH of the sixth temporary mixture at step (viii) to 6.5-7.5 to create a seventh temporary mixture;

(x) mixing 1%-3% by weight a glycerin ingredient into the seventh temporary mixture at step (ix) with the combination of stirring to create a eighth temporary mixture;

(xi) mixing 0.05%-0.1% by weight a vitamin E into the eighth temporary mixture at step (x), with the combination of stirring to create a ninth temporary mixture;

(xii) mixing 0.1%-0.5% by weight a tartrazine ingredient into the ninth temporary mixture at step (xi) with the combination of stirring to create a tenth temporary mixture; wherein the tartrazine ingredient has a concentration of 1%;

(xiii) mixing 5%-7% by weight a $K_2HPO_4$ solution into the tenth temporary mixture at step (xii) with the combination of stirring to create a eleventh temporary mixture; wherein the $K_2HPO_4$ solution has a concentration of 15%;

(xiv) mixing 0.0009%-0.05% by weight a mixture extracts/essential oils into the eleventh temporary mixture at step (xiii) with the combination of stirring to create a twelfth temporary mixture;

(xv) mixing an other ingredient into the twelfth temporary mixture at step (xiv), with the combination of stirring to create a basic mixture; and (xvi) stirring the basic mixture for 1 hour, then adjusting the pH to 6.5-7.5 and leaving it for one day at a temperature of 30° C.-35° C. to create the composition for prevention and treatment of EMS shrimp to replace antibiotics.

Finally, the purpose of the invention is to provide the mixture extracts/essential oils is performed in a specific order from (a') to (d') comprising:

(a') preparing a *Melaleuca alternifolia* extracts/essential oils by:

choosing *Melaleuca alternifolia* leaves that are fresh, not crushed or rotten;

washing and grinding *Melaleuca alternifolia* leaves to a size of 0.2-0.6 mm;

adding 50 g by weight of pureed fresh ingredients into a distillation tank; and adding 500 mL of NaCl solution into the tank, soak the ingredients for about 30 minutes; distilling at 100° C. for 120 minutes to create a liquid mixture of water and essential oil;

extracting the liquid mixture of water and essential oil in the tank, extracted five times, each extraction with 10 mL of diethyl ether;

collecting the entire extract solution and anhydrous the extract solution anhydrous $Na_2SO_4$ salt; and evaporating and recovering the solvent, the extract solution after anhydrous at 55° C. under low pressure to create the *Melaleuca alternifolia* extracts/essential oils;

(b') preparing a Herba Pogostemonis extracts/essential oils by:

choosing Herba Pogostemonis leaves that are fresh, not crushed or rotten; washing the leaves with water and dry at 50° C., and grinding to create a ground leaves powder;

soaking the ground leaves powder in water at a ratio of 1:2, then distilling using a steam distillation system at 100° C. for 150 minutes to create a mixture after distillation; and adding and stirring anhydrous $Na_2SO_4$ to the mixture after distillation until you observe the salt crystals begin to separate, then remove said salt crystals to create the Herba Pogostemonis extracts/essential oils;

(c') preparing a *Illicium verum* extracts/essential oils by:

treating *Illicium verum* fruits to remove mechanical impurities (leaves, twigs, bark, and sand); then soaking in distilled water for about 12-14 hours;

crushing *Illicium verum* fruits after soaking to a size of 0.4-0.6 mm, then soaking with water in a ratio of 1:5, and distilling with saturated steam at 120° C. for 180 minutes to create a mixture after distillation;

settling the mixture after distillation for 24 hours in the separatory funnel to separate the water layer below, recovering the remaining essential oil layer above the separatory funnel, then treating the essential oil layer with anhydrous sodium sulfate salt and filtering to create the *Illicium verum* extracts/essential oils; and (d') mixing homogeneously the *Melaleuca alternifolia* extracts/essential oils with the Herba Pogostemonis extracts/essential oils and the *Illicium verum* extracts/essential oils at a ratio of (1-2):(1-2):(1-2), with the combination of stirring to create the mixture extracts/essential oils.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWINGS

The accompanying drawings, which are incorporated in and form a part of this specification, illustrate embodiments of the invention and, together with the description, serve to explain the principles of the invention.

FIG. 1 is a flowchart illustrating a flowchart of a process of manufacturing composition for prevention and treatment of Early Mortality Syndrome (EMS) shrimp to replace antibiotics in accordance with an exemplary embodiment of the present invention.

DETAILED DESCRIPTION OF THE INVENTION

Reference will now be made in detail to the preferred embodiments, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

In the embodiment of the present invention, percent mass or percentage (%) by weight=(mass of solute/mass of solution)×100%. The unit of mass is usually grams. Mass percent is also known as the correct percentage by weight or w/w %. It should also be noted that the molar mass is also within the meaning of the invention. Molar mass is the total mass of all atoms in a mole of compound. Total all volume percentages add up to 100%.

One embodiment of the invention is now described with reference to FIG. 1, a process of manufacturing composition for prevention and treatment of Early Mortality Syndrome (EMS) shrimp to replace antibiotics 100 ("process 100") in accordance with an exemplary embodiment of the present invention. The process 100 is started with step 101 that preparing a complex composition by mixing a turkey tail mushroom extract (G1) having 10%-15% by weight and a chitosan (G2) having 10%-15% by weight with the combination of stirring at 1200-1500 rpm for 30-40 minutes, then ultrasonic treatment at a frequency of 0.15 to 0.2 kHz combination of stirring at 1200-1500 rpm for 30-50 minutes.

According to the embodiment of the invention, the chitosan (G2) having a minimum deacetylation level of 85% and is extracted from crustacean shells.

According to the preferred embodiment of the present invention, reference to patent application Ser. No. 18/592,551 disclosed the turkey tail mushroom extract is selecting from group consisting of (A) a first turkey tail mushroom component, (B) a second turkey tail mushroom component, (C) a third turkey tail mushroom component, (D) a fourth turkey tail mushroom component, and (E) a fifth turkey tail mushroom component;

wherein the first turkey tail mushroom component is obtained by cultivating *Trametes versicolor* (L.) Pilat;

wherein the second turkey tail mushroom component is obtained by cultivating *Trametes versicolor* (L.) Lioud (1920);

wherein the third turkey tail mushroom component is obtained by cultivating *Trametes sanguinea* (L.) Imazeki;

wherein the fourth turkey tail mushroom component is obtained by cultivating *Trametes versicolor* BRG04; and wherein the fifth turkey tail mushroom component is obtained by cultivating *Pycnoporus sanguineus* (L.: Fr.) Murrill.

According to the embodiment of the invention, each turkey tail mushroom component (A)-(E) is obtained by performing steps (A') to (F'), comprising:

(A') selecting a mature fruiting bodies of the turkey tail mushroom;

(B') harvesting mushroom tissue from the mature fruiting bodies of the turkey tail mushroom with an area ranging from 5-10 mm², inoculating onto a petri dish containing a isolation medium, and then incubating in darkness at 28° C.-30° C. for 4-6 days to obtain a turkey tail mushroom strain;

wherein the isolation medium comprising: potatoes having 200 g/L, glucose having 20 g/L, potassium dihydrogen phosphate ($KH_2PO_4$) having 3 g/L, magnesium sulfate ($MgSO_4$) having 1.5 g/L, and agar having 20 g/L;

(C') inoculating the turkey tail mushroom strain into an erlenmeyer flask containing 100-150 mL of an activation medium, shaking at 120-150 rpm for 4-6 days at 25° C.-27° C. to obtain an activated turkey tail mushroom strain;

wherein the activation medium comprising: glucose having 10 g/L, malt extract having 3 g/L, peptone having 2 g/L, yeast extract having 2 g/L, asparagine having 1 g/L, potassium dihydrogen phosphate ($KH_2PO_4$) having 2 g/L, magnesium sulfate ($MgSO_4$) having 1 g/L, and thiamine having 1 mg/L;

(D') inoculating the activated turkey tail mushroom strain into a biomass growth medium at a ratio of (1-5): 1000, cultivating with agitation at 120-150 rpm for 6-8 days at 25° C.-27° C. to obtain a mixture 1;

wherein the biomass growth medium comprising: glucose having 30 g/L, peptone having 4 g/L, magnesium sulfate ($MgSO_4$) having 0.5 g/L, and potassium dihydrogen phosphate ($KH_2PO_4$) having 1 g/L;

(E') filtering the mixture 1, removing the liquid portion to obtain a turkey tail mushroom biomass; and (F') drying the turkey tail mushroom biomass at 45° C.-50° C. until reaching a moisture content of 10-12% to obtain a turkey tail mushroom biomass component.

According to the preferred embodiment of the present invention, the turkey tail mushroom extract (G1) has a concentration of 0.75%, and chitosan (G2) has a concentration of 0.75%.

According to the preferred embodiment of the present invention, the turkey tail mushroom extract (G1) having 13%-13.5% by weight, and chitosan (G2) having 13%-13.5% by weight.

According to another embodiment of the present invention, the complex composition comprising further an emulsifier ingredient; wherein the emulsifier ingredient is selected from the group consisting of sucrose ester (sucrose ester), monoglyceride (monoglyceride), triglyceride (triglyceride), lecithin, and combinations thereof.

Still with FIG. 1, at step 102, mixing 10%-15% by weight a carboxymethyl cellulose solution (G3) with 10%-15% by weight a alginate solution (G4), and 10%-15% by weight a potassium citrate solution (G5) into the container containing the complex composition at step 101 with the combination of stirring for 30 minutes to create a foundation mixture. It should be noted that the term "admixed/mixed/admixing/mixing" as used in the present invention is understood to mean adding, or reacting, or dissolving homogeneously, or evenly, components in the same solution/mixture. Within the scope of the present invention, the term "homogeneously dissolved" the following meanings of the completely dissolved state or homogenous dissolution of substances in the same mixture/solution.

According to the preferred embodiment of the present invention, the carboxymethyl cellulose solution (G3) has a concentration of 0.375%.

According to the preferred embodiment of the present invention, the alginate solution (G4) has a concentration of 0.375%.

According to the embodiment of the invention, the potassium citrate solution (G5) is prepared by:

(a) preparing citric acid solution has a concentration of 15% by dissolving 1.5 kg of citric acid in the water, then continue adding water to reach the volume of 10 L;

(b) preparing potassium hydroxide (KOH) solution has a concentration of 15% by: dissolving 1.5 kg of KOH in the water, then continue adding water to reach the volume of 10 L; and (c) pouring slowly 1 part citric acid solution at step (a) into 1 part potassium hydroxide solution to create the potassium citrate solution.

According to the preferred embodiment of the present invention, the carboxymethyl cellulose solution (G3) having 13%-13.5% by weight.

According to the preferred embodiment of the present invention, the alginate solution (G4) having 13%-13.5% by weight.

According to the preferred embodiment of the present invention, the potassium citrate solution (G5) having 13%-13.5% by weight.

Within the scope of the present invention, the term "foundation mixture" includes the following meanings:

(a") a foundation mixture is a solution that completely dissolves the complex composition with the three mixing ingredients (G3 to G5) consisting of the carboxymethyl cellulose solution, the alginate solution, and the potassium citrate solution having the correct percentage (%) by weight;

(b") a foundation mixture act as a reactant, allowing the addition of ingredients (G6 to G16) to contribute their chemical and physical properties to create a new preparation having prevention and treatment of Early Mortality Syndrome (EMS) shrimp properties; and (c") a foundation mixture chemically bonds with other complementary ingredients (G6 to G16) including but not limited to ionization reactions, covalent reactions, reducing reactions, replacement reactions, and rearrangement reactions to form a new chemical composition having prevention and treatment of Early Mortality Syndrome (EMS) shrimp properties.

At step 103, mixing 1%-3% by weight a $AgNO_3$ solution (G6) into the foundation mixture at step 102 with the combination of stirring to create a first temporary mixture.

According to the preferred embodiment of the present invention, the $AgNO_3$ solution (G6) has a concentration of 0.37%.

According to the preferred embodiment of the present invention, the $AgNO_3$ solution (G6) having 2.16% by weight.

At step 104, mixing 3%-5% by weight a $Cu(NO_3)_2$ solution (G7) into the first temporary mixture at step 103 with the combination of stirring to create a second temporary mixture.

According to the preferred embodiment of the present invention, the $Cu(NO_3)_2$ solution (G7) has a concentration of 0.723%.

According to the preferred embodiment of the present invention, the $Cu(NO_3)_2$ solution (G7) having 4.2%-4.5% by weight.

At step 105, mixing 0.5%-1% by weight a $Zn(NO_3)_2$ solution (G8) into the second temporary mixture at step 104 with the combination of stirring to create a third temporary mixture.

According to the preferred embodiment of the present invention, the $Zn(NO_3)_2$ solution (G8) has a concentration of 3.085%.

According to the preferred embodiment of the present invention, the $Zn(NO_3)_2$ solution (G8) having 0.9% by weight.

At step 106, mixing 0.05%-0.1% by weight a $Co(NO_3)_2$ solution (G9) into the third temporary mixture at step 105 with the combination of stirring to create a fourth temporary mixture.

According to the preferred embodiment of the present invention, the $Co(NO_3)_2$ solution (G9) has a concentration of 0.746%.

According to the preferred embodiment of the present invention, the $Co(NO_3)_2$ solution (G9) having 0.08% by weight.

At step 107, mixing 0.5%-2% by weight a $Fe(NO_3)_3$ solution (G10) into the fourth temporary mixture at step (vi) with the combination of stirring to create a fifth temporary mixture.

According to the preferred embodiment of the present invention, the $Fe(NO_3)_3$ solution (G10) has a concentration of 2.5%.

According to the preferred embodiment of the present invention, the $Fe(NO_3)_3$ solution (G10) having 1.3%-1.5% by weight.

At step 108, creating a sixth temporary mixture by processing the fifth temporary mixture at step 107 including 02 stages:
  a first stage: stirring the fifth temporary mixture for 1 hour; and a second stage: stirring said processed fifth temporary mixture in first stage at a frequency of every 3 hours and each time stirring for 30 minutes at a speed of 300-500 rpm; wherein the second stage processing time is 24 hours.

At step 109, adjusting pH of the sixth temporary mixture at step 108 to 6.5-7.5 to create a seventh temporary mixture.

At step 110, mixing 1%-3% by weight a glycerin ingredient (G11) into the seventh temporary mixture at step 109 with the combination of stirring to create an eighth temporary mixture.

According to the preferred embodiment of the present invention, the glycerin ingredient (G11) having 2% by weight.

At step 111, mixing 0.05%-0.1% by weight a vitamin E (G12) into the eighth temporary mixture at step (x), with the combination of stirring to create a ninth temporary mixture.

According to the preferred embodiment of the present invention, the vitamin E (G12) having 0.07%-0.08% by weight.

At step 112, mixing 0.1%-0.5% by weight a tartrazine ingredient (G13) into the ninth temporary mixture at step 111 with the combination of stirring to create a tenth temporary mixture.

According to the preferred embodiment of the present invention, the tartrazine ingredient (G13) has a concentration of 1%.

According to the preferred embodiment of the present invention, the tartrazine ingredient (G13) having 0.15%-0.2% by weight.

At step 113, mixing 5%-7% by weight a $K_2HPO_4$ solution (G14) into the tenth temporary mixture at step (xii) with the combination of stirring to create an eleventh temporary mixture.

According to the preferred embodiment of the present invention, the $K_2HPO_4$ solution (G14) has a concentration of 15%.

According to the preferred embodiment of the present invention, the $K_2HPO_4$ solution (G14) having 6.4%-6.8% by weight.

At step 114, mixing 0.0009%-0.05% by weight a mixture extracts/essential oils (G15) into the eleventh temporary mixture at step 113 with the combination of stirring to create a twelfth temporary mixture.

According to the preferred embodiment of the present invention, the mixture extracts/essential oils (G15) having 0.009%-0.05% by weight.

According to the preferred embodiment of the present invention, the mixture extracts/essential oils (G15) is performed in a specific order from (a') to (d') comprising:
  (a') preparing a *Melaleuca alternifolia* extracts/essential oils by:
    choosing *Melaleuca alternifolia* leaves that are fresh, not crushed or rotten;
    washing and grinding *Melaleuca alternifolia* leaves to a size of 0.2-0.6 mm; adding 50 g by weight of pureed fresh ingredients into a distillation tank; and adding 500 mL of NaCl solution into the tank, soak the ingredients for about 30 minutes;
    distilling at 100° C. for 120 minutes to create a liquid mixture of water and essential oil;
    extracting the liquid mixture of water and essential oil in the tank, extracted five times, each extraction with 10 mL of diethyl ether;
    collecting the entire extract solution and anhydrous the extract solution anhydrous $Na_2SO_4$ salt; and
    evaporating and recovering the solvent, the extract solution after anhydrous at 55° C. under low pressure to create the *Melaleuca alternifolia* extracts/essential oils;
  (b') preparing a Herba Pogostemonis extracts/essential oils by:
    choosing Herba Pogostemonis leaves that are fresh, not crushed or rotten;
    washing the leaves with water and dry at 50° C., and grinding to create a ground leaves powder;
    soaking the ground leaves powder in water at a ratio of 1:2, then distilling using a steam distillation system at 100° C. for 150 minutes to create a mixture after distillation; and
    adding and stirring anhydrous $Na_2SO_4$ to the mixture after distillation until you observe the salt crystals begin to separate, then remove said salt crystals to create the Herba Pogostemonis extracts/essential oils;
  (c') preparing a *Illicium verum* extracts/essential oils by:
    treating *Illicium verum* fruits to remove mechanical impurities (leaves, twigs, bark, and sand); then soaking in distilled water for about 12-14 hours;
    crushing *Illicium verum* fruits after soaking to a size of 0.4-0.6 mm, then soaking with water in a ratio of 1:5, and distilling with saturated steam at 120° C. for 180 minutes to create a mixture after distillation;
    settling the mixture after distillation for 24 hours in the separatory funnel to separate the water layer below, recovering the remaining essential oil layer above the separatory funnel, then treating the essential oil layer with anhydrous sodium sulfate salt and filtering to create the *Illicium verum* extracts/essential oils; and (d') mixing homogeneously the *Melaleuca alternifolia* extracts/essential oils with the Herba Pogostemonis extracts/essential oils and the *Illicium verum* extracts/essential oils at a ratio of (1-2):(1-2):(1-2), with the combination of stirring to create the mixture extracts/essential oils.

According to the preferred embodiment of the present invention, the ratio of the *Melaleuca alternifolia* extracts/essential oils with the Herba Pogostemonis extracts/essential oils and the *Illicium verum* extracts/essential oils is 1:1:1.

It should be noted that the term "the mixture extracts/essential oils" in the present invention, an "extracts/essential oil" extracted as an aromatic substance contained in the above-mentioned plants is preferable. The essential oil in a narrow sense obtained by steam distillation from the above plants or dried materials thereof is preferably used as the "extracts/essential oil" in the present invention, but is not limited thereto. For example, oils extracted from the plants by using other methods such as extraction or expression are also included in the "extracts/essential oil" of the present invention as long as they contain essential oil components (such as aromatic substances). As other methods for extracting essential oils from plants, for example, solvent extraction (such as alcohol extraction, organic solvent extraction), oil and fat adsorption extraction (hot enfleurage or cold enfleurage), and supercritical fluid extraction are known. When the steam distillation cannot be applied because of a low essential oil content in the plant and the like, the solvent extraction is often used. Examples of the solvent used for extraction include, but are not limited to, alcohols such as ethanol, methanol, propanol, isopropanol, and butanol, and organic solvents including relatively high polarity solvents such as acetone and low polarity solvents such as hexane. The "extracts/essential oil" in the present invention may be those in which the oil obtained by the above method is further purified and concentrated by using various purification procedures such as hydrophobic or adsorptive chromatography using a support such as porous beads, silica gel, or alumina.

At step 115, mixing an other ingredient (G16) into the twelfth temporary mixture at step (xiv), with the combination of stirring to create a basic mixture.

According to embodiment of the present invention, the other ingredient (G16) is selected from the group consisting of water, EDTA.4 Na, and combinations thereof.

Finally, at step 116, stirring the basic mixture for 1 hour, then adjusting the pH to 6.5-7.5 and leaving it for one day at a temperature of 30° C.-35° C. to create the composition for prevention and treatment of EMS shrimp to replace antibiotics.

It should be noted that when the foundation mixture is admixed to eleven mixing ingredients (G6 to G16) of a predetermined percentage (%) by weight listed in Table 1 below and will be discussed later. However, in an exemplary embodiment of the present invention, each type of mixing ingredients (G6 to G16) is added in a particular order.

It should be noted that when the eleven mixing ingredients (G6 to G16) are not admixed in the specific order described, the final product will not have prevention and treatment of Early Mortality Syndrome (EMS) shrimp properties.

In the embodiment of the present invention, steps 101 to 116 are performed by a magnetic stirrer or stirrer or stirring device, that has been known in previous art so the description of the structure and its operating principle will not be described in detail in the invention.

Another embodiment of the invention is described a composition for prevention and treatment of Early Mortality Syndrome (EMS) shrimp to replace antibiotics 200 ("composition 200") obtain from process 100 creating a basic mixture by mixing a complex composition with mixing ingredients, then stirring the basic mixture for 1 hour, and adjusting the pH to 6.5-7.5 and leaving it for one day at a temperature of 30° C.-35° C.

According to embodiment of the present invention, the complex composition including a turkey tail mushroom extract (G1) and a chitosan (G2).

According to the preferred embodiment of the present invention, the turkey tail mushroom extract (G1) has a concentration of 0.75%, and chitosan (G2) has a concentration of 0.75%.

According to another embodiment of the present invention, the complex composition comprising further an emulsifier ingredient; wherein the emulsifier ingredient is selected from the group consisting of sucrose ester (sucrose ester), monoglyceride (monoglyceride), triglyceride (triglyceride), lecithin, and combinations thereof.

According to embodiment of the present invention, the mixing ingredients consisting of a carboxymethyl cellulose solution (G3) has a concentration of 0.375%, a alginate solution (G4) has a concentration of 0.375%, a potassium citrate solution (G5), a $AgNO_3$ solution (G6) has a concentration of 0.37%, a $Cu(NO_3)_2$ solution (G7) has a concentration of 0.723%, a $Zn(NO_3)_2$ solution (G8) has a concentration of 3.085%, $Co(NO_3)_2$ solution (G9) has a concentration of 0.746%, a $Fe(NO_3)_3$ solution (G10) has a concentration of 2.5%, a glycerin ingredient (G11), a vitamin E (G12), a tartrazine ingredient (G13) has a concentration of 1%, a $K_2HPO_4$ solution (G14) has a concentration of 15%, a mixture extracts/essential oils (G15), and an other ingredient (G16).

According to embodiment of the present invention, the composition 200 comprising:
the turkey tail mushroom extract (G1) having 10%-15% by weight;
the chitosan (G2) having 10%-15% by weight;
the carboxymethyl cellulose solution (G3) having 10%-15% by weight;
the alginate solution (G4) having 10%-15% by weight;
the potassium citrate solution (G5) having 10%-15% by weight;
the $AgNO_3$ solution (G6) having 1%-3% by weight;
the $Cu(NO_3)_2$ solution (G7) having 3%-5% by weight;
the $Zn(NO_3)_2$ solution (G8) having 0.5%-1% by weight;
the $Co(NO_3)_2$ solution (G9) having 0.05%-0.1% by weight;
the $Fe(NO_3)_3$ solution (G10) having 0.5%-2% by weight;
the glycerin ingredient (G11) having 1%-3% by weight;
the vitamin E (G12) having 0.05%-0.1% by weight;
the tartrazine ingredient (G13) having 0.1%-0.5% by weight;
the $K_2HPO_4$ solution (G14) having 5%-7% by weight;
the mixture extracts/essential oils (G15) having 0.0009%-0.05% by weight; wherein the mixture extracts/essential oils is obtained by mixing homogeneously a *Melaleuca alternifolia* extracts/essential oils with a Herba Pogostemonis extracts/essential oils and a *Illicium verum* extracts/essential oils at a ratio of (1-2):(1-2):(1-2); and the rest is other ingredient (G16); wherein the other ingredient is selected from the group consisting of water, EDTA.4 Na, and combinations thereof.

According to the preferred embodiment of the present invention, the composition 200 comprising:

the turkey tail mushroom extract (G1) having 13%-13.5% by weight;

the chitosan (G2) having 13%-13.5% by weight;

the carboxymethyl cellulose solution (G3) having 13%-13.5% by weight;

the alginate solution (G4) having 13%-13.5% by weight;

the potassium citrate solution (G5) having 13%-13.5% by weight;

the $AgNO_3$ solution (G6) having 2.16% by weight;

the $Cu(NO_3)_2$ solution (G7) having 4.2%-4.5% by weight;

the $Zn(NO_3)_2$ solution (G8) having 0.9% by weight;

the $Co(NO_3)_2$ solution (G9) having 0.08% by weight;

the $Fe(NO_3)_3$ solution (G10) having 1.3%-1.5% by weight;

the glycerin ingredient (G11) having 2% by weight;

the vitamin O (G12) having 0.07%-0.08% by weight;

the tartrazine ingredient (G13) having 0.15%-0.2% by weight;

the $K_2HP_4$ solution (G14) having 6.4%-6.8% by weight;

the mixture extracts/essential oils (G15) having 0.009%-0.05% by weight; wherein the mixture extracts/essential oils is obtained by mixing homogeneously the *Melaleuca alternifolia* extracts/essential oils with the Herba Pogostemonis extracts/essential oils and the *Illicium verum* extracts/essential oils at a ratio of 1:1:1; and the rest is other ingredient (G16); wherein the other ingredient is selected from the group consisting of water, EDTA.4 Na, and combinations thereof.

TABLE 1

Mixed ingredients to creating the composition 200 according to the process 100 in accordance with an exemplary embodiment of the present invention

| Note | Name of | Percentage (%) | Optimal percentage (%) |
|---|---|---|---|
| G1 | The turkey tail mushroom extract | 10%-15% | 13%-13.5% |
| G2 | The chitosan | 10%-15% | 13%-13.5% |
| G3 | The carboxymethyl cellulose 0.375% | 10%-15% | 13%-13.5% |
| G4 | The alginate solution 0.375% | 10%-15% | 13%-13.5% |
| G5 | The potassium citrate | 10%-15% | 13%-13.5% |
| G6 | The $AgNO_3$ solution 0.37% | 1%-3% | 2.16% |
| G7 | The $Cu(NO_3)_2$ solution 0.723% | 3%-5% | 4.2%-4.5% |
| G8 | The $Zn(NO_3)_2$ solution 3.085% | 0.5%-1% | 0.9% |
| G9 | The $Co(NO_3)_2$ solution 0.746% | 0.05%-0.1% | 0.08% |
| G10 | The $Fe(NO_3)_3$ solution 2.5% | 0.5%-2% | 1.3%-1.5% |
| G11 | The glycerin ingredient | 1%-3% | 2% |
| G12 | The vitamin E | 0.05%-0.1% | 0.07%-0.08% |
| G13 | The tartrazine ingredient 1% | 0.1%-0.5% | 0.15%-0.2% |
| G14 | The $K_2HPO_4$ solution 15% | 5%-7% | 6.4%-6.8% |
| G15 | The mixture extracts/essential oils | 0.0009%-0.05% | 0.009%-0.05% |
| G16 | The other ingredient | rest | rest |

The example is made according to the embodiment of the present invention, the composition 200 is created by process 100 with a capacity of 150 kg/batch including five examples listed in Table 2 below.

Prepare the solutions, including:

preparing the carboxymethyl cellulose solution 0.375% by dissolving 3.750 kg of the carboxymethyl cellulose solution 2% into the water, and make up to 20 kg of the carboxymethyl cellulose solution 0.375%;

preparing the alginate solution 0.375% by dissolving 3.750 kg of the alginate solution 2% into the water, and make up to 20 kg of the alginate solution 0.375%; and preparing the $K_2HPO_4$ solution 15% by dissolving 1.5 kg of $K_2HPO_4$ into the water, and make up to 10 kg of the $K_2HPO_4$ solution 15%.

TABLE 2

Mixed ingredients of the composition 200 according to five examples in accordance with exemplary embodiment of the present invention

| Name of | | Unit (kg) | | | | |
|---|---|---|---|---|---|---|
| | | Example 1 | Example 2 | Example 3 | Example 4 | Example 5 |
| The complex composition | The turkey tail mushroom extract | 20 | 18 | 22.5 | 21 | 22 |
| | The chitosan | 20 | 18 | 22.5 | 21 | 22 |
| | The carboxymethyl cellulose solution 0.375% | 20 | 18 | 22.5 | 21 | 22 |
| | The alginate solution 0.375% | 20 | 18 | 22.5 | 21 | 22 |
| | The potassium citrate solution 15% | 20 | 18 | 22.5 | 21 | 22 |
| | The $AgNO_3$ solution 0.37% | 3.240 | 3 | 3.5 | 3.3 | 3.5 |
| | The $Cu(NO_3)_2$ solution 0.723% | 6.370 | 6 | 6.5 | 6.6 | 6.3 |
| | The $Zn(NO_3)_2$ solution 3.085% | 1.350 | 1.2 | 1.4 | 1.5 | 1.1 |
| | The $Co(NO_3)_2$ solution 0.746% | 0.120 | 0.1 | 0.2 | 0.15 | 0.2 |
| | The $Fe(NO_3)_3$ solution 2.5% | 2.165 | 2 | 2.5 | 2.4 | 2.3 |
| | The glycerin ingredient | 3 | 2.5 | 3.5 | 3.3 | 3. |
| | The vitamin E | 0.116 | 0.1 | 0.2 | 0.15 | 0.3 |
| | The Tartrazine ingredient 1% | 0.250 | 0.2 | 0.3 | 0.33 | 0.35 |
| | The $K_2HPO_4$ solution 15% | 10 | 9 | 11.25 | 10.5 | 11 |
| The mixture extracts/ essential oils | *Melaleuca alternifolia* oil | 0.00046 | 0.0005 | 0.0006 | 0.0014 | 0.0004 |
| | *Herba Pogostemonis* oil | 0.00046 | 0.0005 | 0.0012 | 0.0007 | 0.0008 |
| | *Illicium verum* oil | 0.00046 | 0.0010 | 0.0006 | 0.0007 | 0.0008 |
| The other ingredient | | rest | rest | rest | rest | rest |

Testing the safety and effectiveness of the composition 200 obtained by the process 100 in accordance with an exemplary embodiment of the present invention.

Test subjects: 2-week-old shrimp with an average weight of 1-1.5 g/fish, domesticated in composite tanks for 2 weeks, quarantined shrimp do not carry pathogens.

Shrimp farming conditions: the shrimp pond is 1,000 in$^2$; the pond is washed with clean water, then disinfected with chlorine 30 mg/L, and dried in the sun for about 5 hours before use. Control water quality in shrimp ponds to meet technical specifications including: temperature from 20° C.-30° C., salinity from 15%-25%, clarity from 25-35 cm, pH from 7.5-8.5, alkalinity from 100-180 mg/l, dissolved oxygen content from 3.5-5.5 mg/l, $NH_3$ content less than 0.1 mg/l, H-2S content less than 0.03 mg/l; with a stocking density of 80 fish/in$^2$.

The test sample is the composition according to example 1 listed Table 2 ("product 300"), and the control sample used normal shrimp food.

The bacterial strain *V. parahaemolyticus* causes Early Mortality Syndrome (EMS).

1) Testing the safety of shrimp using product 300 by arranging in two 1,000 m$^2$ shrimp ponds, one pond for shrimp to use product 300 and one pond for using normal shrimp food; Feed continuously for 14 days, feed four times/day, at 8:00, 11:00, 14:00, and 18:00 with a food amount equal to 2%-5% of body weight; Continuous aeration 24 hours/day; Monitor and evaluate survival rate within 14 days. The results are presented in Table 3 below.

TABLE 3

The results evaluate the survival rate of shrimp in accordance with exemplary embodiment of the present invention

| | The survival rate of shrimp in 14 days (%) | | |
|---|---|---|---|
| Experimental | 3 days | 7 days | 14 days |
| Product 300 | 100 | 100 | 100 |
| The control sample | 100 | 100 | 100 |

Based on Table 3, after 14 days of experiment, there were no deaths or abnormal signs on the shrimp. Therefore, shrimp using product 300 gives good growth rate and high survival rate. This test result shows that using product 300 is safe for shrimp.

2) Testing the ability to prevent early mortality syndrome (EMS) using product 300.

The test sample: shrimp used product 300 for seven consecutive days, then were experimentally infected on the 8th day of culture by directly soaking shrimp in V. *Parahaemolyticus* bacterial solution at a concentration of 10$^6$ cfu/mL for 30 minutes. Then, the shrimp were continued to use product 300 two times, each lasting seven consecutive days.

The control sample: shrimp used normal shrimp food for seven consecutive days, then were experimentally infected on the 8th day of culture by directly soaking shrimp in V. *Parahaemolyticus* bacterial solution at a concentration of 10$^6$ cfu/mL for 30 minutes. Then, the shrimp were continued to use normal shrimp food two times, each lasting seven consecutive days. Monitor and evaluate survival rate within 14 days; The results are presented in Table 4 below.

TABLE 4

The results evaluate the survival rate of shrimp after infected with *V. Parahaemolyticus* bacteria for 14 days

| | The survival rate of shrimp in 14 days (%) | | |
|---|---|---|---|
| Experimental | 3 days | 7 days | 14 days |
| Product 300 | 76 | 63 | 47 |
| The control sample | 32 | 28 | 0 |

Based on Table 4, shrimp began to show signs of pathology and died on the 3rd day after infection. The survival rate gradually decreased from day 3 to day 14 after infection; the experiment ended on day 14, and shrimp died completely in the control treatment; in the treatment using product 300, the survival rate reached 47%. The results show that using product 300 is highly effective in preventing early mortality syndrome (EMS).

3) Testing the ability to treat diseases to early mortality syndrome (EMS) using product 300.

The test sample: experimentally infected on the 8th day of culture by directly soaking shrimp in V. *Parahaemolyticus* bacterial solution at a concentration of 10$^6$ cfu/mL for 30 minutes. Then, the shrimp were continued to use product 300 two times, each lasting seven consecutive days.

The control sample: experimentally infected on the 8th day of culture by directly soaking shrimp in V. *Parahaemolyticus* bacterial solution at a concentration of 10$^6$ cfu/mL for 30 minutes. Then, the shrimp were continued to use normal shrimp food two times, each lasting seven consecutive days. Monitor and evaluate survival rate within 14 days; The results are presented in Table 5 below.

TABLE 5

The results evaluate the death rate of shrimp after infected with *V. Parahaemolyticus* bacteria for 14 days

| | The death rate of shrimp in 14 days (%) | | |
|---|---|---|---|
| Experimental | 3 days | 7 days | 14 days |
| Product 300 | 32 | 40 | 48 |
| The control sample | 45 | 63 | 95 |

Based on Table 5, the shrimp began to die on the 3rd day after infection in the treatments using product 300 and the control treatment. The mortality rate of shrimp in the treatments gradually increased on the following days, and all treatments stopped dying on day seven until the end of the experiment (14 days). The cumulative mortality rate increased, the highest on day 14, up to 95% in the control treatment. In experimental treatments using product 300, the cumulative mortality rate increased highest on day 14 at 48%; the mortality rate was lower than in control treatments. The results show that using product 300 is highly effective in treating early mortality syndrome (EMS).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including" when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A process of manufacturing a composition for prevention and treatment of Early Mortality Syndrome (EMS) shrimp to replace antibiotics comprising:
   (i) preparing a complex composition by mixing a turkey tail mushroom (*Trametes versicolor*) extract having 10%-15% by weight and a chitosan having 10%-15% by weight with the combination of stirring at 1200-1500 rpm for 30-40 minutes, then ultrasonic treatment at a frequency of 0.15 to 0.2 kHz combination of stirring at 1200-1500 rpm for 30-50 minutes;
      wherein the chitosan having a minimum deacetylation level of 85% and is extracted from crustacean shells;
      wherein the turkey tail mushroom (*Trametes versicolor*) extract is selecting from group consisting of (A) a first turkey tail mushroom (*Trametes versicolor*) component, (B) a second turkey tail mushroom (*Trametes versicolor*) component, (C) a third turkey tail mushroom (*Trametes versicolor*) component, (D) a fourth turkey tail mushroom (*Trametes versicolor*) component, and (E) a fifth turkey tail mushroom (*Trametes versicolor*) component;
      the first turkey tail mushroom component is obtained by cultivating *Trametes versicolor* (L.) Pilat;
      the second turkey tail mushroom component is obtained by cultivating *Trametes versicolor* (L.) Lioud (1920);
      the third turkey tail mushroom component is obtained by cultivating *Trametes sanguinea* (L.) Imazeki;
      the fourth turkey tail mushroom component is obtained by cultivating *Trametes versicolor* BRG04; and
      the fifth turkey tail mushroom component is obtained by cultivating *Pycnoporus sanguineus* (L.: Fr.) Murrill;
      wherein each turkey tail mushroom (*Trametes versicolor*)_component (A)-(E) is obtained by performing steps (A') to (F'), comprising:
   (A') selecting a mature fruiting body of the turkey tail mushroom (*Trametes versicolor*);
   (B') harvesting mushroom tissue from the mature fruiting body of the turkey tail mushroom (*Trametes versicolor*) with an area ranging from 5-10 mm$^2$, inoculating onto a petri dish containing a isolation medium, and then incubating in darkness at 28° C.-30° C. for 4-6 days to obtain a turkey tail mushroom (*Trametes versicolor*) strain;
      wherein the isolation medium comprising: potatoes having 200 g/L, glucose having 20 g/L, potassium dihydrogen phosphate ($KH_2PO_4$) having 3 g/L, magnesium sulfate ($MgSO_4$) having 1.5 g/L, and agar having 20 g/L;
   (C') inoculating the turkey tail mushroom (*Trametes versicolor*) strain into an erlenmeyer flask containing 100-150 mL of an activation medium, shaking at 120-150 rpm for 4-6 days at 25° C.-27° C. to obtain an activated turkey tail mushroom (*Trametes versicolor*) strain;
      wherein the activation medium comprising: glucose having 10 g/L, malt extract having 3 g/L, peptone having 2 g/L, yeast extract having 2 g/L, asparagine having 1 g/L, potassium dihydrogen phosphate ($KH_2PO_4$) having 2 g/L, magnesium sulfate ($MgSO_4$) having 1 g/L, and thiamine having 1 mg/L;
   (D') inoculating the activated turkey tail mushroom (*Trametes versicolor*) strain into a biomass growth medium at a ratio of (1-5):1000, cultivating with agitation at 120-150 rpm for 6-8 days at 25° C.-27° C. to obtain a mixture 1;
      wherein the biomass growth medium comprising: glucose having 30 g/L, peptone having 4 g/L, magnesium sulfate ($MgSO_4$) having 0.5 g/L, and potassium dihydrogen phosphate ($KH_2PO_4$) having 1 g/L;
   (E') filtering the mixture 1, removing the liquid portion to obtain a turkey tail mushroom (*Trametes versicolor*) biomass; and
   (F') drying the turkey tail mushroom (*Trametes versicolor*) biomass at 45° C.-50° C. until reaching a moisture content of 10-12% to obtain a turkey tail mushroom (*Trametes versicolor*) component;
   (ii) mixing 10%-15% by weight a carboxymethyl cellulose solution with 10%-15% by weight a alginate solution, and 10%-15% by weight a potassium citrate solution into the container containing the complex composition at step (i) with the combination of stirring for 30 minutes to create a foundation mixture;

wherein the carboxymethyl cellulose solution has a concentration of 0.375%;
wherein the alginate solution has a concentration of 0.375%;
wherein the potassium citrate solution is prepared by:
(a) preparing citric acid solution has a concentration of 15% by dissolving 1.5 kg of citric acid in the water, then continue adding water to reach the volume of 10 L;
(b) preparing potassium hydroxide (KOH) solution has a concentration of 15% by: dissolving 1.5 kg of KOH in the water, then continue adding water to reach the volume of 10 L; and
(c) pouring slowly 1 part citric acid solution at step (a) into 1 part potassium hydroxide solution to create the potassium citrate solution;
(iii) mixing 1%-3% by weight a $AgNO_3$ solution into the foundation mixture at step (ii) with the combination of stirring to create a first temporary mixture; wherein the $AgNO_3$ solution has a concentration of 0.37%;
(iv) mixing 3%-5% by weight a $Cu(NO_3)_2$ solution into the first temporary mixture at step (iii) with the combination of stirring to create a second temporary mixture; wherein the $Cu(NO_3)_2$ solution has a concentration of 0.723%;
(v) mixing 0.5%-1% by weight a $Zn(NO_3)_2$ solution into the second temporary mixture at step (iv) with the combination of stirring to create a third temporary mixture; wherein the $Zn(NO_3)_2$ solution has a concentration of 3.085%;
(vi) mixing 0.05%-0.1% by weight a $Co(NO_3)_2$ solution into the third temporary mixture at step (v) with the combination of stirring to create a fourth temporary mixture; wherein the $Co(NO_3)_2$ solution has a concentration of 0.746%;
(vii) mixing 0.5%-2% by weight a $Fe(NO_3)_3$ solution into the fourth temporary mixture at step (vi) with the combination of stirring to create a fifth temporary mixture; wherein the $Fe(NO_3)_3$ solution has a concentration of 2.5%;
(viii) creating a sixth temporary mixture by processing the fifth temporary mixture at step
(vii) including 02 stages:
a first stage: stirring the fifth temporary mixture for 1 hour; and
a second stage: stirring said processed fifth temporary mixture in first stage at a frequency of every 3 hours and each time stirring for 30 minutes at a speed of 300-500 rpm; wherein the second stage processing time is 24 hours;
(ix) adjusting pH of the sixth temporary mixture at step (viii) to 6.5-7.5 to create a seventh temporary mixture;
(x) mixing 1%-3% by weight a glycerin ingredient into the seventh temporary mixture at step (ix) with the combination of stirring to create a eighth temporary mixture;
(xi) mixing 0.05%-0.1% by weight a vitamin E into the eighth temporary mixture at step (x), with the combination of stirring to create a ninth temporary mixture;
(xii) mixing 0.1%-0.5% by weight a tartrazine ingredient into the ninth temporary mixture at step (xi) with the combination of stirring to create a tenth temporary mixture;
wherein the tartrazine ingredient has a concentration of 1%;
(xiii) mixing 5%-7% by weight a $K_2HPO_4$ solution into the tenth temporary mixture at step (xii) with the combination of stirring to create a eleventh temporary mixture; wherein the $K_2HPO_4$ solution has a concentration of 15%;
(xiv) mixing 0.0009%-0.05% by weight a mixture extracts/essential oils into the eleventh temporary mixture at step (xiii) with the combination of stirring to create a twelfth temporary mixture; wherein the mixture extracts/essential oils is performed in a specific order from (a') to (d') comprising:
(a') preparing a *Melaleuca alternifolia* extracts/essential oils by:
choosing *Melaleuca alternifolia* leaves that are fresh, not crushed or rotten;
washing and grinding *Melaleuca alternifolia* leaves to a size of 0.2-0.6 mm;
adding 50 g by weight of pureed fresh ingredients into a distillation tank; and
adding 500 mL of NaCl solution into the tank, soak the ingredients for about 30 minutes;
distilling at 100° C. for 120 minutes to create a liquid mixture of water and essential oil;
extracting the liquid mixture of water and essential oil in the tank, extracted five times, each extraction with 10 mL of diethyl ether;
collecting the entire extract solution and anhydrous the extract solution anhydrous $Na_2SO_4$ salt; and
evaporating and recovering the solvent, the extract solution after anhydrous at 55° C. under low pressure to create the *Melaleuca alternifolia* extracts/essential oils;
(b') preparing a Herba Pogostemonis extracts/essential oils by:
choosing Herba Pogostemonis leaves that are fresh, not crushed or rotten;
washing the leaves with water and dry at 50° C., and grinding to create a ground leaves powder;
soaking the ground leaves powder in water at a ratio of 1:2, then distilling using a steam distillation system at 100° C. for 150 minutes to create a mixture after distillation; and
adding and stirring anhydrous $Na_2SO_4$ to the mixture after distillation until you observe the salt crystals begin to separate, then remove said salt crystals to create the Herba Pogostemonis extracts/essential oils;
(c') preparing a *Illicium verum* extracts/essential oils by:
treating *Illicium verum* fruits to remove mechanical impurities (leaves, twigs, bark, and sand); then soaking in distilled water for about 12-14 hours;
crushing *Illicium verum* fruits after soaking to a size of 0.4-0.6 mm, then soaking with water in a ratio of 1:5, and distilling with saturated steam at 120° C. for 180 minutes to create a mixture after distillation;
settling the mixture after distillation for 24 hours in the separatory funnel to separate the water layer below, recovering the remaining essential oil layer above the separatory funnel, then treating the essential oil layer with anhydrous sodium sulfate salt and filtering to create the *Illicium verum* extracts/essential oils;
(d') mixing homogeneously the *Melaleuca alternifolia* extracts/essential oils with the Herba Pogostemonis extracts/essential oils and the *Illicium verum* extracts/essential oils at a ratio of (1-2):(1-2):(1-2), with the combination of stirring to create the mixture extracts/essential oils;

(xv) mixing an other ingredient into the twelfth temporary mixture at step (xiv), with the combination of stirring to create a basic mixture; and (xvi) stirring the basic mixture for 1 hour, then adjusting the pH to 6.5-7.5 and leaving it for one day at a temperature of 30° C.-35° C. to create the composition for prevention and treatment of EMS shrimp to replace antibiotics.

2. The process of claim 1, wherein at step (i) the turkey tail mushroom (*Trametes versicolor*) extract having 13%-13.5% by weight, and chitosan having 13%-13.5% by weight.

3. The process of claim 1, wherein at step (ii) the carboxymethyl cellulose solution having 13%-13.5% by weight, the alginate solution having 13%-13.5% by weight, and the potassium citrate solution having 13%-13.5% by weight.

4. The process of claim 1, wherein at step (iii) the $AgNO_3$ solution having 2.16% by weight.

5. The process of claim 1, wherein at step (iv) the $Cu(NO_3)_2$ solution having 4.2%-4.5% by weight.

6. The process of claim 1, wherein at step (v) the $Zn(NO_3)_2$ solution having 0.9% by weight.

7. The process of claim 1, wherein at step (vi) the $Co(NO_3)_2$ solution having 0.08% by weight.

8. The process of claim 1, wherein at step (vii) the $Fe(NO_3)_3$ solution having 1.3%-1.5% by weight.

9. The process of claim 1, wherein at step (x) the glycerin ingredient having 2% by weight.

10. The process of claim 1, wherein at step (xi) the vitamin E having 0.07%-0.08% by weight.

11. The process of claim 1, wherein at step (xii) the tartrazine ingredient having 0.15%-0.2% by weight.

12. The process of claim 1, wherein at step (xiii) the $K_2HPO_4$ solution having 6.4%-6.8% by weight.

13. The process of claim 1, wherein at step (xiv) the mixture extracts/essential oils having 0.009%-0.05% by weight.

14. The process of claim 1, wherein the other ingredient is selected from the group consisting of water, EDTA.4 Na, and combinations thereof.

15. The process of claim 1, wherein at step (i) the turkey tail mushroom (*Trametes versicolor*) extract has a concentration of 0.75%, and the chitosan has a concentration of 0.75%.

16. The process of claim 1, wherein the complex composition comprising further an emulsifier ingredient; wherein the emulsifier ingredient is selected from the group consisting of sucrose ester (sucrose ester), monoglyceride (monoglyceride), triglyceride (triglyceride), lecithin, and combinations thereof.

* * * * *